United States Patent [19]

Mullis, Sr. et al.

[11] Patent Number: 5,048,354
[45] Date of Patent: Sep. 17, 1991

[54] DEVICE FOR SAMPLING A CIRCULATING FLUID

[76] Inventors: James E. Mullis, Sr.; James E. Mullis, Jr., both of Unit #8, 980 Pacific Gate, Mississauga, Ontario, Canada, L5T 1Y1

[21] Appl. No.: 463,503

[22] Filed: Jan. 11, 1990

[51] Int. Cl.$^5$ ............................................. G01N 1/20
[52] U.S. Cl. ............................. 73/863.25; 73/863.61; 73/863.86; 340/607
[58] Field of Search ........... 73/863.23, 863.24, 863.25, 73/863.81–863.86, 863.61, 38; 340/607

[56] References Cited

U.S. PATENT DOCUMENTS

| | | | |
|---|---|---|---|
| 2,843,077 | 7/1958 | Leefer | 340/607 X |
| 3,010,583 | 11/1961 | Kenyon | 73/863.23 X |
| 3,056,379 | 10/1962 | Thomas | 340/607 |
| 3,310,984 | 3/1967 | Swanson | 73/863.23 |
| 3,325,010 | 6/1967 | Sackett | 73/38 X |
| 3,413,855 | 12/1968 | Bloom | 73/38 X |
| 3,429,186 | 2/1969 | Price et al. | 73/863.86 X |
| 3,459,176 | 8/1969 | Leonard | 73/863.23 X |
| 3,488,993 | 1/1970 | Raynor | 73/863.23 |
| 3,934,238 | 1/1976 | Pavlou | 340/607 X |
| 4,114,427 | 9/1978 | Iguchi et al. | 73/863.83 X |
| 4,117,717 | 10/1978 | Isley | 73/38 |
| 4,240,912 | 12/1980 | Stumpf et al. | 73/863.25 X |
| 4,245,669 | 1/1981 | Schmidt | 137/550 |
| 4,263,805 | 4/1981 | Isley et al. | 73/38 |
| 4,361,028 | 11/1982 | Kamiya et al. | 73/23.33 |
| 4,380,168 | 4/1983 | Ibe | 73/40.5 R |
| 4,925,627 | 5/1990 | Johnson | 73/863.82 X |

Primary Examiner—Tom Noland
Attorney, Agent, or Firm—Smart & Biggar

[57] ABSTRACT

A device is provided for sampling the contents of a pressurized circulating fluid system of a machine. The device is incorporated in a parallel fluid circuit and comprises a housing with an inlet to, and outlet from, a cavity. A filter is received within the cavity. When the filter becomes clogged, a differential pressure sensor provides an indication for an operator to close the inlet to the filter cavity, drain the cavity by means of a valve, and then remove the filter by removing a plug. The drained cavity fluid and filter may then be shipped to a lab for testing and the filter replaced and the inlet to the cavity reopened.

9 Claims, 1 Drawing Sheet

DEVICE FOR SAMPLING A CIRCULATING FLUID

FIELD OF THE INVENTION

This invention relates to a device for sampling the contents of a pressured circulating fluid system.

DESCRIPTION OF RELATED ART

To ensure the long life of machinery, it is desirable to periodically analyse the state of fluid circulating in the machinery. In this regard, it is known to introduce a valve in the fluid system from which a fluid sample may be removed for testing. Particulate matter trapped in the system filter may provide further information on the state of the fluid in the system and, accordingly, it is also known to forward the system filter for testing.

Testing of the system filter suffers the drawback that filters in heavy equipment are large and awkward to handle. Further, one must be satisfied with an analysis at periods dictated by the routine changing of the system filter. This is for the reason that to require more frequent changings to permit more frequent analysis would result in additional down time for the equipment.

Accordingly, there remains a need for apparatus to facilitate the testing of fluid circulating in a machine which preferably avoids machine down time.

SUMMARY OF THE INVENTION

Accordingly, there is provided a device for sampling the contents of a pressurized circulating fluid system comprising: a housing having a cavity, an inlet to said cavity for receiving fluid from a pressurized circulating fluid system, and an outlet from said cavity; a filter seated in said cavity and interposed between said inlet and said outlet; means for sensing the pressure differential between said inlet and said outlet; and valve means for draining said cavity to obtain fluid for analysis and to facilitate removal of said filter.

In the drawings which illustrate example embodiments of the invention:

DESCRIPTION OF THE PREFERRED EMBODIMENT

Figure 1:
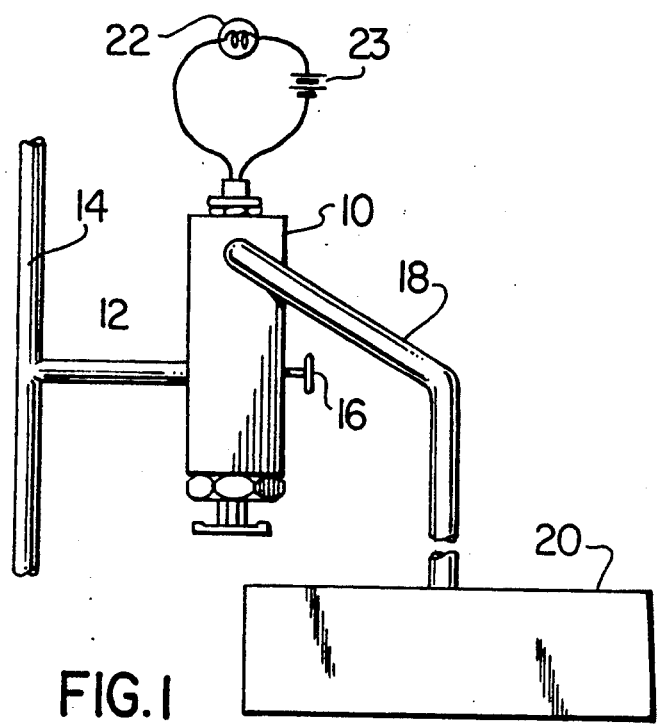
FIG. 1 is a partially schematic side view of a portion of a pressurized circulating fluid system made in accordance with the present invention.

Referring to FIG. 1, a feeder line 12 is tapped off the main fluid line 14 of the circulating fluid system of a machine. The feeder line feeds the fluid sampling device 10 detailed in FIG. 2. The sampling device 10 incorporates a shut off valve, the handle for which is shown at 16. An outlet line 18 runs between the fluid sampling device 10 and the fluid sump 20 of the machine. Thus, the fluid sampling device 10 is in a fluid circuit which is in parallel with the main circulating fluid system of the machine. An indicating light 22 and battery 23 are operatively connected to the sampling device by wire 24.

Figure 2:
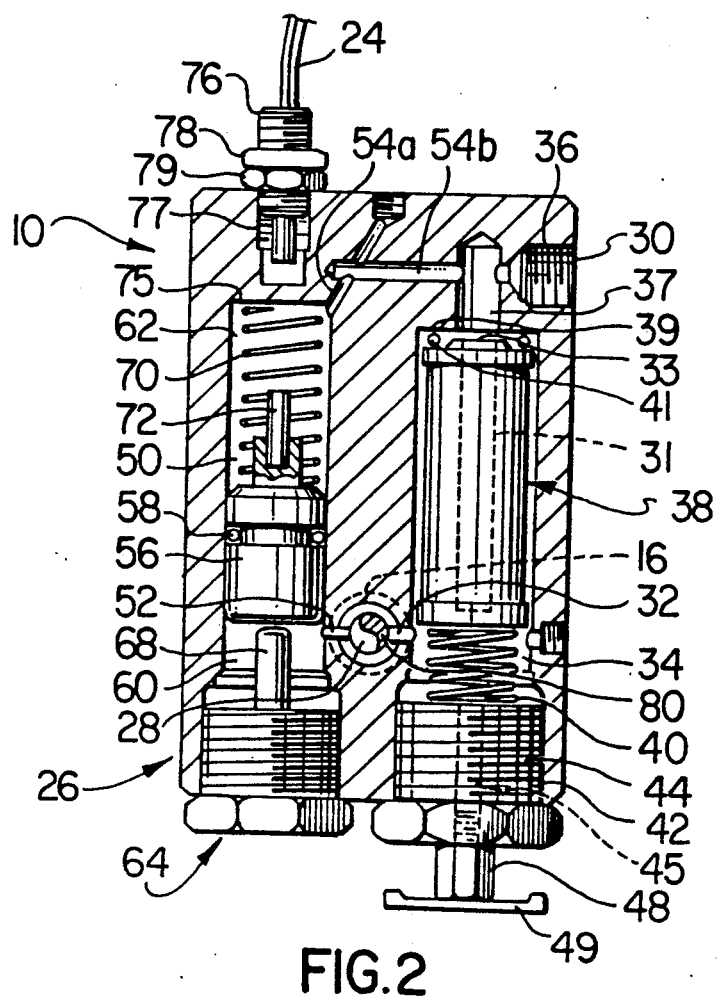
FIG. 2 is a cross sectional view of a fluid sampling device made in accordance with the invention.

Turning to FIG. 2, the sampling device 10 is seen to comprise a housing 26 having an inlet 28 (for connection to feeder line 12 of FIG. 1) and an outlet 30 (for connection to outlet line 18 of FIG. 1). An inlet fluid passageway 32 extends between the inlet and a filter cavity 34, proximate plug 44. An outlet fluid passageway 36 extends between the reduced diameter end 37 of the cavity and the outlet 30.

Cavity 34 is closed by threaded plug 44 which is threaded into threaded opening 42 of the cavity. Opening 42 is sized to permit passage of a filter 38. Filter 38 is located within filter cavity 34 with the open end 33 of the core 31 of the filter directed toward reduced diameter end 37 of the filter cavity. The filter is seated against shoulder 39 of the cavity by spring 40 which acts against one end of the plug 44 and the filter. O-ring 41 provides a fluid seal between the end of the filter and shoulder 39. Thus, the filter is interposed between the inlet 28 and the outlet 30. The threaded plug 44 has a valve therein comprising central bore 45 sealed by cap 48 which is threaded into a threaded end of the bore. A handle 49 is affixed to cap 48.

A differential pressure sensing chamber 50 within the housing communicates with the inlet 28 (and hence the upstream side of the filter 38) through passageway 52 and with the outlet 30 (and hence the downstream side of the filter) through passageways 54a, 54b and 36. A threaded plug 64 closes the upstream end of the chamber 50. A post 68 extends into the chamber from plug 64 to just downstream of passage 52. A piston 56 is received within the chamber 50. A piston O-ring 58 provides a fluid seal between the piston and chamber 50. The piston 56 divides the chamber 50 into an upstream portion 60 and a downstream portion 62.

Spring return 70 located in the downstream portion 62 of the chamber 50 urges the piston 56 toward post 68. A magnet 72 is affixed to the downstream end of the piston. It should be noted that passageway 52 can never be closed off by piston 56 since post 68 extends to just downstream of the passageway.

A magnetically actuated proximity switch 74 is affixed to threaded shaft 76. Shaft 76 is threaded into threaded opening 77 of housing 26 which is proximate the downstream end 75 of chamber 50. The threaded shaft 76 is held in place by nuts 78 and 79. The proximity switch 74 is connected to wire 24 to indicating light 22 and battery 23 (of FIG. 1).

Shut off valve handle 16 connects to valve element 80 in inlet 28.

In operation, in an embodiment of the invention wherein the fluid is oil, pressurized oil enters inlet 28 of the sampling device 10 through feeder line 12. So long as shut off valve element 80 is in an open position, oil flows through fluid passageway 32 to filter cavity 34. The oil flows through the wall of the filter to its core 31 and then exits through outlet 30 to outlet line 18. The filter 38 traps any particulate matter present in the oil.

The oil pressure in the sampling device 10 upstream and downstream of filter 38 is communicated to the upstream 60 and downstream 62 portions of pressure differential sensing chamber 50 by passageways 52 and 54a, 54b, respectively. Pressurized oil in the upstream portion 60 of chamber 50 urges piston 56 toward the downstream end 75 of the chamber 50. The spring 70 and oil pressure in the downstream portion 62 of the chamber provide a counteracting force. This counteracting force seats piston on post 68 until the filter clogs sufficiently that the reduced downstream pressure and the force provided by the spring do not counteract the upstream pressure, whereupon the piston moves toward end 75 to a new equilibrium point. When piston 56 reaches a pre-set distance from the proximity switch 74, the magnetic flux from magnet 72 actuates the proximity switch and lamp 22 is illuminated, signalling the operator to sample the oil.

The differential pressure at which the lamp is illuminated can be selected by altering the distance shaft 76 is threaded into threaded opening 77, which adjusts the proximity of the proximity switch 74 to end 75 of chamber 50. Further, this differential pressure may be controlled by selecting a spring 70 having an appropriate spring constant.

When the operator has received a signal indicating that a sample should be taken, valve element 80 is positioned to close passageway 32 to isolate the filter cavity 34 from the oil circulating system and from the differential pressure chamber 50. It should be noted that this does not interrupt the oil circulating system thus allowing for continued operation of the machine throughout the sampling process. Handle 49 is then turned, to remove cap 48 and drain filter cavity 34 into an oil sample vial which the operator holds beneath bore 45. Plug 44 can then be removed in order to allow removal of spring 40 and filter 38. The filter and oil sample may then be forwarded for analysis. A fresh filter may be inserted into the filter cavity with spring 40 following and the plug 44 and cap 48 replaced whereupon valve element 80 may be reopened which brings the sampling device into operation once more.

It will be obvious to one skilled in the art that the proximity switch 74 could be modified to close when the piston moved a preset distance away from switch 74 in which case the proximity switch would be mounted at the other end of chamber 50. It will also be apparent the valve in plug 44 for draining cavity 34 could be replaced by a separate valve with a valve bore communicating with cavity 34 proximate the base of the cavity.

We claim:

1. A device for sampling the contents of a pressurized circulating fluid system comprising:
   (a) a housing having a cavity, an inlet to said cavity for receiving fluid from the pressurized circulating fluid system, and an outlet from said cavity;
   (b) a filter seated in said cavity and interposed between said inlet and said outlet;
   (c) means for sensing the pressure differential between said inlet and said outlet; and
   (d) valve means for draining said cavity to obtain fluid for analysis and to facilitate removal of said filter.

2. The device of claim 1 including shut off valve means for closing said inlet to said cavity.

3. The device of claim 2 wherein said cavity comprises an opening to the exterior of said housing sized to permit passage of said filter, said opening being sealed by removable plug means.

4. The device of claim 3 wherein said valve means for draining comprise a bore through said plug means sealed by a removable cap.

5. A device as claimed in claim 4 wherein said means for sensing the pressure differential between said inlet and said outlet comprises:
   (a) a differential pressure sensing chamber having passageways communicating with said inlet and said outlet;
   (b) a piston within said sensing chamber dividing said chamber into a portion in fluid communication with said inlet and a portion in fluid communication with said outlet;
   (c) means to urge said piston toward said inlet; and
   (d) signal means responsive to the position of said piston within said sensing chamber.

6. In a pressurized circulating fluid system, a parallel fluid circuit having a device for sampling the contents of a pressurized circulating fluid system comprising:
   (a) a housing;
   (b) a fluid passageway within said housing having an inlet to receive fluid from the pressurized circulating fluid system and an outlet wherefrom fluid leaves said housing;
   (c) a filter seated in a cavity within said fluid passageway and interposed between said inlet and said outlet;
   (d) means for sensing the pressure differential between said inlet and said outlet; and
   (e) valve means for draining said cavity to obtain fluid for analysis and to facilitate removal of said filter, said parallel circuit further comprising a shut-off valve for cutting off said pressurized circulating fluid system from said fluid passageway.

7. The system of claim 6 wherein said cavity comprises an opening to the exterior of said housing sized to permit passage of said filter, said opening being sealed by removable plug means.

8. The system of claim 7 wherein said valve means for draining comprises a bore through said plug means sealed by a removable cap.

9. A system as claimed in claim 8 wherein said means for sensing the pressure differential between said inlet and said outlet comprises:
   (a) a differential pressure sensing chamber having passageways communicating with said inlet and said outlet;
   (b) a piston within said sensing chamber dividing said chamber into a portion in fluid communication with said inlet and a portion in fluid communication with said outlet;
   (c) means to urge said piston toward said inlet; and
   (d) signal means responsive to the position of said piston within said sensing chamber.

* * * * *